(12) United States Patent
Schwann et al.

(10) Patent No.: US 12,257,061 B2
(45) Date of Patent: Mar. 25, 2025

(54) DEVICE FOR EXPLORING THE VISUAL SYSTEM

(71) Applicant: UNIVERSITE DE LORRAINE, Nancy (FR)

(72) Inventors: Raymund Schwann, Villiers-les-Nancy (FR); Valérie Louis-Dorr, Lay Saint Christophe (FR); Thomas Schwitzer, Nancy (FR)

(73) Assignee: UNIVERSITE DE LORRAINE, Nancy (FR)

( * ) Notice: Subject to any disclaimer, the term of this patent is extended or adjusted under 35 U.S.C. 154(b) by 966 days.

(21) Appl. No.: 16/975,945

(22) PCT Filed: Feb. 26, 2019

(86) PCT No.: PCT/FR2019/000023
§ 371 (c)(1),
(2) Date: Aug. 26, 2020

(87) PCT Pub. No.: WO2019/166704
PCT Pub. Date: Sep. 6, 2019

(65) Prior Publication Data
US 2020/0405172 A1 Dec. 31, 2020

(30) Foreign Application Priority Data
Feb. 28, 2018 (FR) ....................................... 1800175

(51) Int. Cl.
*A61B 5/398* (2021.01)
*A61B 3/00* (2006.01)
(Continued)

(52) U.S. Cl.
CPC .............. *A61B 5/398* (2021.01); *A61B 3/005* (2013.01); *A61B 3/156* (2013.01); *A61B 5/0002* (2013.01);
(Continued)

(58) Field of Classification Search
CPC ......... A61B 5/398; A61B 3/005; A61B 3/156; A61B 5/0002; A61B 5/7405; A61B 2090/502; A61B 2562/0209
See application file for complete search history.

(56) References Cited

U.S. PATENT DOCUMENTS 5,726,916 A * 3/1998 Smyth .................. A61B 5/6814
351/210
9,579,060 B1 * 2/2017 Lisy ..................... A61B 5/4803
(Continued)

FOREIGN PATENT DOCUMENTS

CA 2824972 A1 2/2015
CN 1960670 A 5/2007
(Continued)

OTHER PUBLICATIONS

Japanese Office Action for corresponding Japanese Patent Application No. 2020-545125 dated Mar. 4, 2022.
(Continued)

*Primary Examiner* — Linda C Dvorak
*Assistant Examiner* — Abigail Bock
(74) *Attorney, Agent, or Firm* — Greer, Burns & Crain, Ltd.

(57) ABSTRACT

A device for exploring the visual system, comprising portable viewing equipment having at least one viewing screen configured to be placed facing at least one eye of a person. The viewing equipment comprises sealing lips surrounding the viewing screens and having a free edge intended to be applied against the skin of the person, this free edge comprising at least one electrode for measuring the electrical potential. The device also comprises at least one free electrode for measuring the electrical potential, which free electrode is linked by a connecting wire to a connector carried by the viewing equipment, between one of the
(Continued)

viewing screens and the free edge of the sealing lips surrounding this screen.

15 Claims, 3 Drawing Sheets

(51) Int. Cl.
  *A61B 3/15*    (2006.01)
  *A61B 5/00*    (2006.01)
  *A61B 90/50*    (2016.01)

(52) U.S. Cl.
  CPC ...... *A61B 5/7405* (2013.01); *A61B 2090/502* (2016.02); *A61B 2562/0209* (2013.01)

(56) References Cited

U.S. PATENT DOCUMENTS

| | | | |
|---|---|---|---|
| 2006/0145032 A1* | 7/2006 | Hsieh | F16L 3/23 |
| | | | 248/65 |
| 2009/0058660 A1 | 3/2009 | Torch | |
| 2015/0029463 A1 | 1/2015 | Hetling et al. | |
| 2016/0270656 A1* | 9/2016 | Samec | A61B 3/1216 |
| 2017/0017083 A1 | 1/2017 | Samec et al. | |
| 2017/0150897 A1 | 6/2017 | Komaki | |
| 2018/0103838 A1 | 4/2018 | Green | |
| 2018/0103917 A1* | 4/2018 | Kim | A61B 5/291 |

FOREIGN PATENT DOCUMENTS

| | | |
|---|---|---|
| CN | 101185016 A | 5/2008 |
| CN | 104080394 A | 10/2014 |
| CN | 106880475 A | 6/2017 |
| CN | 106943142 A | 7/2017 |
| CN | 107427209 A | 12/2017 |
| CN | 107582053 A | 1/2018 |
| JP | 201187609 A | 8/2012 |
| JP | 201793984 A | 11/2018 |
| KR | 101318987 B1 | 10/2013 |
| WO | 2005094667 A2 | 10/2005 |
| WO | 2016116933 A1 | 7/2016 |
| WO | 2017099318 A1 | 6/2017 |
| WO | 2019052239 A1 | 3/2019 |

OTHER PUBLICATIONS

Chinese Office Action and Supplementary Search for corresponding Chinese Patent Application No. 201980016071.1 dated Nov. 29, 2021.
Chinese Office Action for corresponding Chinese Patent Application No. 201980016071.1 dated Apr. 20, 2021 and English Translation.
International Search Report; priority document.

* cited by examiner

DEVICE FOR EXPLORING THE VISUAL SYSTEM

CROSS-REFERENCES TO RELATED APPLICATIONS

This application claims the benefit of the International Application No. PCT/FR2019/000023, filed on Feb. 26, 2019, and of the French patent application No. 1800175 filed on Feb. 28, 2018, the entire disclosures of which are incorporated herein by way of reference.

FIELD OF THE INVENTION

The present invention relates to a device that makes it possible to carry out exploration of the visual system.

In particular, the present invention relates to a device of this kind that implements portable display equipment.

BACKGROUND OF THE INVENTION

Various types of exploration of the visual system are known. These explorations are often used in order to carry out ophthalmic examinations in order to detect different physiological ocular characteristics of a person, or in order to explore the person's central nervous system. These explorations can thus be used for research, or to allow for diagnosis of various conditions.

Among these explorations of the visual system, in particular the electroretinogram is known, often denoted by the abbreviation ERG, which is an electrophysiological examination that makes it possible, in particular, to diagnose some functional conditions of the retina or particular disorders of the central nervous system.

An examination of this kind is carried out in specialized clinical neurophysiology or ophthalmology services, using a device known as an electroretinograph.

In order for the person's pupils to be in the dilation state required for performing the examination, said person is placed in the dark for an adjustment period of twenty to thirty minutes, before an operator places on their face, using low-power lighting, the electrodes required for the examination. These electrodes comprise one or more measuring electrodes which can be placed on the cornea, on the skin of the bottom eyelid, in the conjunctival cul-de-sac, or below the bottom eyelid, and reference electrodes which are usually placed on the forehead, on the canthus, and on each earlobe.

After these electrodes have been positioned, the person is placed in front of the electroretinograph which is a device allowing for emission of stimulations such as flashes of light or light stimulations having a variable geometry, preferably full field, and for measuring, via the various electrodes, the electrophysiological response of the retina to the light stimulations.

An examination of this kind is expensive, and is generally carried out only in a hospital environment or in a specialized center. Indeed, the electroretinograph is a bulky and expensive device which must be placed in darkness for the entire duration of the examination. It is also necessary, in order to carry out this examination, to provide a room that is reserved for accustoming the person to the darkness. Finally, a specific electrical installation must also be implemented for connecting the electroretinograph.

Consequently, the electroretinograms are carried out only for specific indications. It would, however, be advantageous to perform these examinations more frequently, in order to make it possible to detect particular retinal disorders, or indeed particular neurological or psychological disorders, earlier or more systematically.

US 2017/0017083 discloses the use of augmented reality display equipment for carrying out a series of ophthalmic examinations, including the electroretinogram. However, this document does not describe the means and processes to be implemented in order to actually carry out an examination of this kind under good conditions.

SUMMARY OF THE INVENTION

An object of the present invention is to overcome these drawbacks of the prior art.

In particular, an object of the present invention is to allow for exploration of the visual system to be carried out in easier conditions and at a lower cost than the solutions of the prior art.

A particular object of the invention is to allow for electroretinograms to be carried out in adjusted and perfectly controlled conditions.

These objects, and others that will emerge more clearly in the following, are achieved by means of a device for exploration of the visual system, comprising portable display equipment comprising at least one display screen intended to be placed in front of at least one eye of a person. According to the invention, the display equipment comprises closure lips that surround at least the display screen or one of the display screens and comprise a free edge that is intended to be applied against the person's skin, around his eye or his eyes in front of the screen, the free edge comprising at least one electrode for measuring the electrical potential, which electrode is intended to be applied against the person's skin, and the device comprises at least one free electrode for measuring the electrical potential, which electrode is connected, by means of a connecting wire, to a connector that is borne by the display equipment, between one of the display screens and the free edge of the closure lips surrounding the screen.

The device according to the invention thus makes it possible to simultaneously perfectly isolate the person's eyes from the external light, perform light stimulations in front of the eyes, and measure the electrophysiological responses to the stimulations. It thus makes it possible to carry out an electroretinogram in a particularly simple manner.

According to an advantageous embodiment, the display equipment comprises two display screens which are each intended to be placed in front of one of the eyes of the person, and the closure lips surround each of the screens.

It is thus possible to carry out differentiated light stimulations for the two eyes, each eye being isolated from the stimulations intended for the other eye.

Advantageously, the closure lips comprise means for retaining the optical lenses in front of at least one of the screens.

It is thus possible to easily carry out observations of people's visual system requiring corrections of their sight.

The device advantageously comprises a retaining strap for the display equipment, which strap is intended to be passed behind the head of the person, the retaining strap bearing at least one electrode for measuring the electrical potential.

It is thus possible to easily measure the electrophysiological response of the occipital cortex to the light stimulations while the electroretinogram is being performed.

According to an advantageous embodiment, the connector is borne by the display equipment, by means of a wire of variable length.

It is thus possible to facilitate the installation of the free electrodes on the person, the connection of the electrodes to the display equipment, and the installation of the display equipment.

The device preferably comprises an acquisition system that is capable of synchronizing the data measured by the electrodes with the visual stimulations produced by the screen(s).

The acquisition system advantageously comprises means for amplifying the signals measured by the electrodes, means for filtering the signals, and means for converting the analog signals into digital signals.

According to an advantageous feature, the device comprises an audio output that is capable of communicating instructions to the person.

The audio output is provided, for example, by loudspeakers.

Advantageously, the device comprises at least one input peripheral.

A peripheral of this kind may, for example, be formed by a control lever, carried by the person wearing the display equipment, or by a microphone associated with a voice-recognition program.

According to a preferred embodiment, the device comprises at least one computer that is remote from the display equipment, and means for communicating between the display equipment and the remote computer.

The remote computer can, for example, perform the processing and analysis of the data collected by the display equipment. The communication means can, in particular, be radio or wired means.

According to a particularly advantageous embodiment, the portable display equipment comprises at least one semi-reflective surface that is intended to be placed in front of at least one eye of the person, and at least one illumination and/or image capture device, pointed in the direction of the eye, by means of a reflection on the semi-reflective surface.

The illumination and/or image capture devices can thus be pointed at the person's eye, in order to observe it or to carry out examinations there, without impairing the eye's vision of the screen.

The semi-reflective surface is advantageously formed by the surface of the screen.

According to another advantageous embodiment, the semi-reflective surface is placed in front of the surface of the screen.

Advantageously, the illumination and/or image capture device is a camera.

In this case, the device can advantageously follow the position of the eye.

According to another advantageous solution, the illumination and/or image capture device comprises a laser emitter and means for capturing the reflection, on the eye, of the laser beam emitted by the laser emitter.

In this case, the device can advantageously carry out examinations such as optical coherence tomography.

BRIEF DESCRIPTION OF THE DRAWINGS

Other objects and advantages of the invention will emerge more clearly from reading the following description of preferred embodiments, given merely by way of simple representational and non-limiting example, and accompanied by figures in which.

DETAILED DESCRIPTION OF THE PREFERRED EMBODIMENTS

Figure 1:
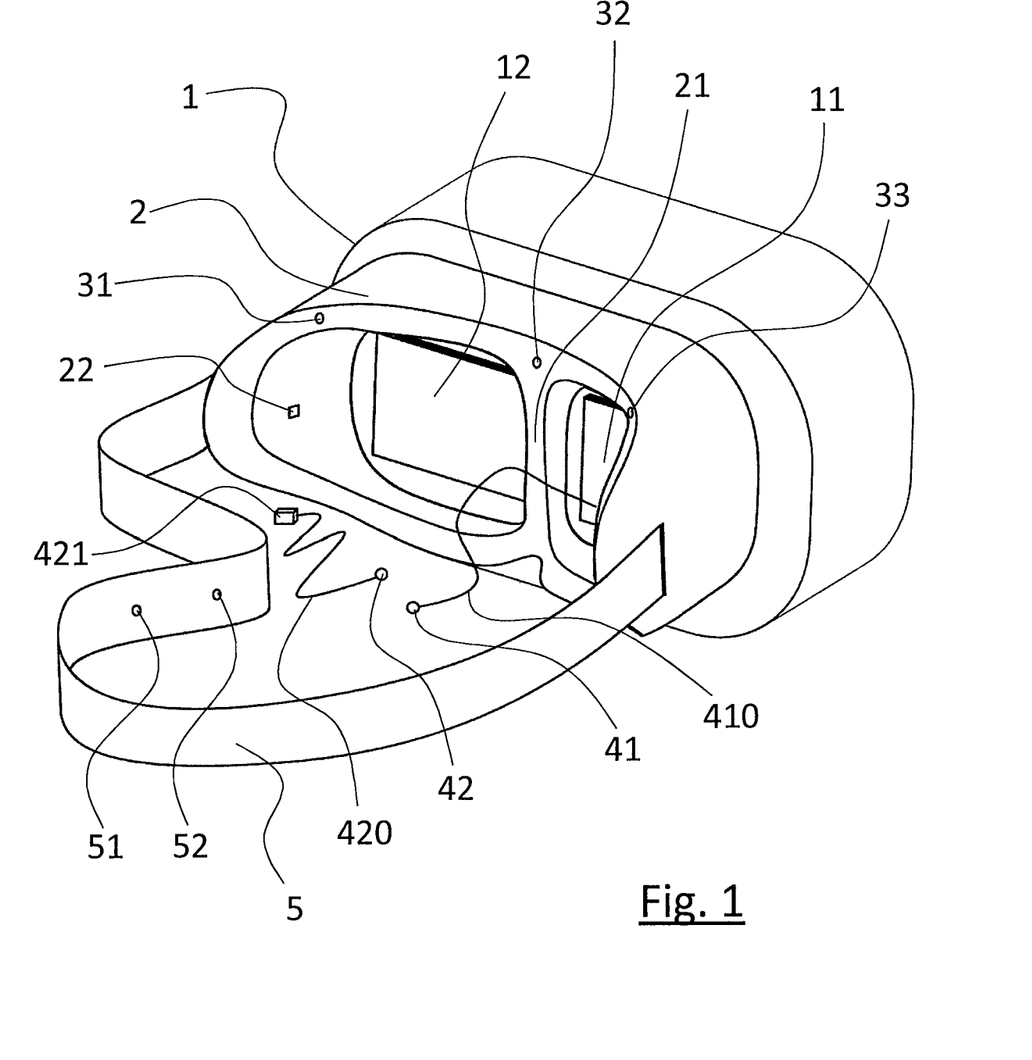
FIG. 1 shows display equipment that is suitable for carrying out exploration of the visual system.

FIG. 1 shows portable display equipment that is suitable, according to an embodiment of the invention, for carrying out exploration of the visual system.

In the present description, the term "portable display equipment" denotes equipment that can be worn on a person's face and allows the person to view images on one or more screens placed at a fixed position in front of their eyes, independently of the person's movements. Display equipment of this kind can thus make it possible to view different images with each of the person's eyes, for example images having different viewing angles of the same virtual object. Equipment of this kind is known per se and is often integrated in a helmet, a mask, or a pair of glasses. It is often used to make it possible to view virtual reality, or three-dimensional images.

The device shown in FIG. 1 thus comprises a mask 1 forming portable display equipment that is specially adapted for carrying out exploration of the visual system. The mask 1 comprises a right-hand display screen 11 which is positioned so as to cover the person's right-hand eye, and a left-hand display screen 12 which is positioned so as to cover the person's left-hand eye.

A strap 5, which is attached to the mask 1, to the right of the right-hand display screen 11 and to the left of the left-hand display screen 12, is intended to make it possible to retain the mask 1 on the person's face. The strap 5 can advantageously be a resilient strap, and the length thereof is preferably adjustable, according to known methods, in order to allow for good adjustment and good retention of the mask 1 on the face.

Advantageously, the mask 1 also comprises closure lips 2 that surround the two display screens 11 and 12 and are intended to be placed against the person's skin, around their eyes. The closure lips 2 thus make it possible to isolate the person's eyes from all outside light, usually referred to as parasitic light or interference light, which does not originate from one of the display screens 11 and 12. The device for exploration of the visual system thus makes it possible to perfectly control the light that can be seen by the person's eyes, independently of the lighting conditions of the room in which the person is, which allows for exploration of the visual system in perfectly controlled conditions.

Advantageously, the closure lips 2 have a central shank 21 that is intended to be placed against the person's forehead and nose, and makes it possible to isolate each of the person's eyes from the light emitted by the display screen placed in front of the other eye. The central shank 21 makes it possible to perfectly control the light arriving at each of the person's eyes, which makes it possible to perform exploration of the visual system implementing stimulations of each eye independently.

Owing to the presence of the closure lips, the mask 1 can place the person's eyes in complete darkness, irrespective of the lighting level in the room in which they are. The mask 1, worn by the person, thus allows for the person's adjustment to the darkness for twenty to thirty minutes, and then for the electroretinogram to be carried out, without any need for the person to be placed in a darkened room.

According to a first possible embodiment, the closure lips 2 may be formed by a wall of flexible material, such as flexible rubber, a silicon, or any other appropriate flexible material. The wall is preferably dark in color and of a sufficient thickness to prevent the passage of light. During use, the free edge of the wall comes into contact on the person's skin, deforming in order to fit the shape of the person's face.

According to another possible embodiment, the closure lips are formed of flexible foam, preferably dark in color and sufficiently thick to prevent the passage of light. The foam can be covered by a flexible plastic film or a fabric. During use, the free edge of the lips comes into contact on the person's skin, deforming in order to fit the shape of the person's face.

It should be noted that, in other possible embodiments of the invention, the mask 1 may have a single screen, positioned so as to cover both of the person's eyes. In this case, the closure lips 2 may surround the single screen, without having a central shank. It is also possible for a central shank to extend in front of the screen, in order to separate it into two portions that are each positioned in front of one of the person's eyes.

Preferably, the portions of the closure lips 2 intended to be in contact with the person's skin may comprise one or more reference electrodes 31, 32 and 33. The electrodes may advantageously be dry-contact electrodes. Thus, when the person wears the mask 1, the reference electrodes 31, 32 and 33 are placed directly against their skin, without the need to install them separately from the mask 1 or to glue them. In the embodiment shown, the lips 2 comprise three reference electrodes 31, 32 and 33. However, the number and the position of the reference electrodes may be different in other embodiments of the invention.

Measurement Electrodes.

The measurement electrodes 41 and 42, or ocular electrodes, which make it possible to carry out an electroretinogram, must be placed in contact with or close to the person's eyes. Preferably, in order to obtain a signal having a good signal-to-noise ratio, the electrodes must be placed in contact with the eye, often under one of the person's eyelids. When the placement on the eye is impossible or complicated, it is also possible to place the electrodes on an eyelid, for example on the person's bottom eyelid. The electrodes must be placed by an operator before the mask 1 is positioned on the person's eyes.

Advantageously, the measurement electrodes 41 and 42 are connected to the mask 1 by wires 410 and 420, respectively. As is shown in FIG. 1, the end of the wire 420 which is not connected to the electrode 42 is connected to a plug 421, the shape of which is complementary to a socket 22 forming a connector. The socket 22 is positioned, in the mask 1, in the space inside the closure lips 2, i.e., between one of the display screens and the free edge of the closure lips 2 surrounding the screen. Preferably, as shown in FIG. 1, the socket 22 is located in the inside face of one of the lips 2. In other embodiments, the socket may be located to the side of the screen 11 or 12, in the zone surrounded by the lips 2.

Thus, when a person wears the mask 2, the wire 420 does not pass between the person's skin and the closure lip 2. There is suddenly no local raising of the lip 2, which could allow for external light to penetrate towards the person's eye. This particular connection of the electrode 42 thus contributes to the perfect control of the light reaching the eye, and the conditions for exploration of the person's eye.

The wire 410 of the measurement electrode 41 is advantageously connected in an identical manner, in a suitable connector placed in the space located inside the closure lips 2.

Figure 2:
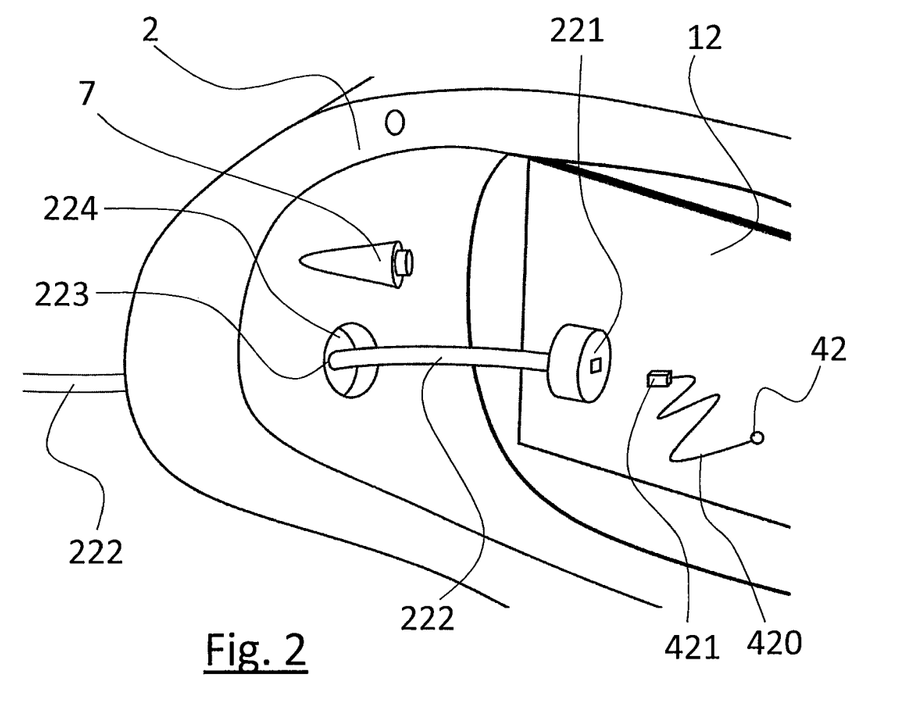
FIG. 2 is a detailed view of display equipment according to a particular embodiment.

FIG. 2 is a detailed view of a mask 1, forming portable display equipment, which is adapted according to a particular embodiment. This figure thus shows a portion of the closure lips 2 of the mask, in which a cylindrical hole 223 has been pierced in order to allow a wire 222 to pass through. The end of the wire, located inside the space defined by the closure lips, bears a socket 221 that forms a connector in which the plug 421, connected to the electrode 42 by the wire 420, can be connected.

The length of the wire 222 which is located inside the space defined by the closure lips 2 makes it possible to more easily carry out the connection of the plug 421 in the socket 221, once the operator has installed the electrode 42 on the person's eye, and before the mask 1 is positioned on the person's face. Once the connection has been carried out, and the mask 1 is positioned on the person's face, it is possible to pull the wire 222, from the outside of the mask 1, until the socket 221 comes into position in a space 224 intended for receiving it, on the inside face of the closure lip 2, around the hole 223. Thus, the wire 222 does not stay in the space located inside the closure lips 2, and does not impair the person's view of the screen 12 of the mask 1. Furthermore, the hole 223 is advantageously of a diameter substantially equal to the diameter of the wire 222, such that the light from the outside cannot pass through the lip 2 via said hole 223.

Figure 4:
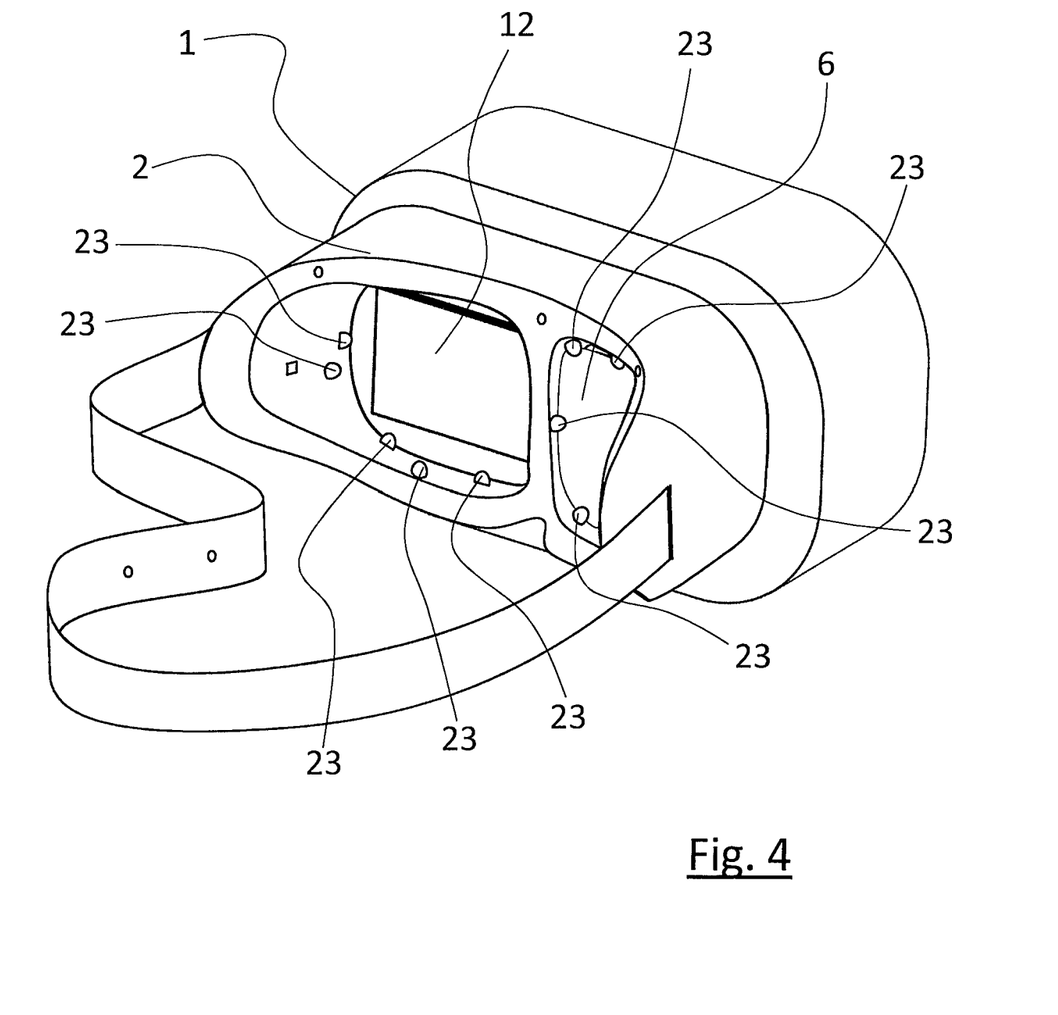
FIG. 4 shows display equipment according to a variant of the invention.

FIG. 4 shows a mask 1 forming portable display equipment according to a variant of the invention. According to this variant, the inside face of the lip 2 comprises lugs 23 that allow for optical lenses 6, or corrective lenses, to be retained in front of the screens 11 and 12. In the variant carried out, only one lens 6 has been placed in front of the screen 11. Preferably, the person using the mask 1, or an operator, can place lenses 6, having a correction suitable for the person's eyes, into the lugs 23, in order for the person to clearly see the images projected by the screens 11 and 12.

In a particularly advantageous manner, the mask 1 may comprise means that make it possible to measure the adjusted correction. Thus, the mask 1 may comprise means that make it possible to carry out an analysis, by means of refractometry, of the person's eye, in order to determine the correction that needs to be provided.

According to yet another variant, the screens 11 and 12 may be adjusted so as to display images that simulate the necessary optical correction in order for the person to see said images clearly. Such an adjustment of the screens 11 and 12 is known, per se, to a person skilled in the art.

Using portable display equipment according to the invention advantageously makes it possible to carry out an electroretinogram in a simpler manner than in the case of the solutions of the prior art.

In order to carry out said test, an operator must first position the measurement electrodes, either in contact with the person's eye or in contact with their bottom eyelid. After having installed said measurement electrodes, the operator can connect the wires of the electrodes to connectors located in the mask 1, and position the mask on the person's eyes, ensuring that the wires of the measurement electrodes are indeed placed inside the closure lips and do not impair the person's view of the screens 11 and 12.

During this installation of the mask 1, the reference electrodes 31, 32 and 33 borne by the closure lips 2 are positioned so as to be directly in contact with the person's skin, around their eyes.

Once the mask 1 is installed, the person's eyes are kept in darkness by the mask, the screens 11 and 12 and the closure lips 2 isolating them from the outside light. The person can thus be kept in darkness for a period of from twenty to thirty minutes in order to adjust to the darkness, resulting in a stable pupil dilation.

Following the step of adjustment to the darkness, the electroretinogram itself is performed, without the person needing to remove the mask or to change position. In order to do this, the display screens 11 and 12 display visual stimulations or flashes of light. These stimulations may be monocular, i.e., relevant to just one of the person's eyes, via one of the screens 11 or 12, or binocular, by means of simultaneous stimulation of both eyes, carried out simultaneously by the screens 11 and 12. In the embodiments in which the mask 1 has just a single screen, extending in front of both the person's eyes, monocular stimulation may be achieved, for example, by placing an opaque shield in front of one of the person's eyes. The opaque shield may be retained, for example, by lugs 23 provided for retaining optical lenses.

The visual stimulations may be those which are used in the known examination protocols. They may thus consist of flashes of light, or displaying specified patterns, either stable or variable, at a specified distance from the person's eyes.

In the case of monocular stimulation, the distance between the image and the person's eye may be simulated by means of adjusting the size of the image displayed on the screen. In the case of binocular stimulation, the distance may be simulated by means of adjusting the size of the image and by offsetting the viewing angle, between the images displayed on the screens 11 and 12, allowing for stereoscopic vision.

Advantageously, within the context of a stimulation protocol corresponding to a multifocal electroretinogram, the images displayed may change at an increased rhythm, in order to stimulate different zones of the retina in sequence. In the same way, the protocols may implement visual stimulations made up of black-and-white or colored images, in order to stimulate different retinal neurons. In the same way, using portable display equipment also allows for protocols implementing light stimulations in the form of three dimensional images.

An acquisition system, advantageously borne by the mask 1, makes it possible to synchronize the data measured by the electrodes, with visual stimulations produced by the screens 11 and 12, in order to obtain useful electroretinogram measurements. The acquisition system preferably comprises means for amplifying the signals measured by the electrodes, means for filtering the signals in order to suppress the irrelevant components thereof, and means for converting the analog signals into digital signals.

The amplification means may, for example, comprise an instrumentation and isolation pre-amplifier, the gain of which is at least 80 dB at a high common-mode rejection ratio (greater than 100 dB), and a scaling amplifier, the gain of which is adjusted prior to conversion. The filtering means may comprise a high-pass filter, the cutoff frequency of which is approximately 0.2 Hz, for rejecting the continuous and very slightly variable components, a low-pass filter for eliminating the high-frequency disturbances above 300 Hz, and digital filters implemented after the analog-to-digital conversion, for rejecting potentials at 50 Hz resulting from the alternative electrical current of the area. The conversion means may comprise an analog-to-digital converter having eight analog paths, at 12-bit conversion, and the sampling frequency of which can be fixed at 4,096 samples per second.

Since the data have been processed, in this way, by the acquisition system, they can then be sent to processing software that is capable of carrying out interpretations of the data. According to a preferred embodiment, the processing software is executed on a computer remote from the mask 1. In this case, the mask 1 may comprise means for communication, for example via radio, allowing it to send the data, measured and processed by the acquisition system, to the computer on which the processing software is executed.

Advantageously, software can be implemented in the mask 1, or in a computer connected to the mask 1, in order to manage the series of steps necessary for carrying out the exploration of the visual system. Thus, the software can manage an audio output formed by a loudspeaker, headphones, or by a plug allowing for connection of a loudspeaker or of headphones, capable of communicating, to the person using the mask 1, usage instructions for correctly carrying out the exploration. The software can likewise control the display of information, either on one of the screens 11 and 12, for it to be visible to the person wearing the mask 1, or on another screen that is borne by the mask 1 and is positioned so as to be visible to a person not wearing the mask, such as an operator.

According to an advantageous solution, the person wearing the mask 1 can interact with the software, via a suitable input peripheral. The input peripheral may be formed, for example, by a control lever (usually referred to as a joystick), which can be connected to the mask 1 via a connection cable or via a radio link, for example the Bluetooth protocol. The input peripheral may also be formed by a microphone, for example placed in the mask 1, making it possible to capture the person's voice. In this case, the software may comprise voice-recognition means which make it possible, for example, to recognize simple instructions from the user.

The software can also carry out a preliminary analysis of the data collected and processed by the acquisition system, in order to verify the coherence of the data measured by the electrodes. It can thus verify, before any visual stimulation, that the electrodes are measuring a signal, indicating that they are correctly positioned. It can then implement the series of visual stimulations and analyze the data collected and processed by the acquisition system, in order to verify that the data are not disturbed by measurement anomalies, such as a movement of the person's eyes or eyelids. If such anomalies appear, the software can repeat a series of stimulations, in order to attempt to obtain, for the stimulations, a result free of anomalies.

Thus, the software may coordinate the successive or simultaneous performance of a series of steps or examinations, without the need for intervention by an operator. In the case of an electroretinogram, for example, the software can automatically start the stimulation steps, following the step of adjustment to the darkness.

The portable display equipment according to the invention may advantageously comprise components that allow it to carry out other examinations aiming at exploration of the visual or neurological system.

For example, in a particularly advantageous embodiment, the retaining strap 5 may comprise one or more electrodes, for example two right-hand 51 and left-hand 52 occipital electrodes, intended for measuring the electrophysiological potentials in the populations of occipital neurons located at the rear of the skull, just above the nape of the neck. These electrodes may advantageously be dry-contact electrodes. The data measured by the occipital electrodes 51 and 52 can advantageously be collected and processed by the acquisition system that collects the data originating from the reference electrodes and the ocular electrodes. Preferably, the acquisition system simultaneously collects the data originating from the retinal electrodes 41 and 42 and the occipital electrodes 51 and 52, in order to synchronously measure the response of the occipital cortex to light stimulations perceived by the retina.

In another possible embodiment, the display equipment may comprise means for measuring the person's visual field, for example prior to performing the electroretinogram. In order to achieve this, the screens 11 and 12 may display light points at successive specified positions, but which cannot be predicted by the person, in and outside of their visual field, the person indicating whether they perceive these points, for example by means of a control lever or by means of oral instructions, perceived by a microphone and interpreted by a software of the display equipment.

The display equipment can usefully also comprise exploration means that make it possible to carry out optical coherence tomography (usually designated by the abbreviation "OCT"), retinophotography, retinorefractometry, or pupillometry. Pupillometry can thus be carried out before an electroretinogram, in order to verify that the pupil is sufficiently dilated to carry out the electroretinogram, and during or after the electroretinogram in order to verify that the dilation is remaining constant. It is also possible to detect the position of the eye and/or eyelids (an operation commonly designated as "eye tracking"), for example in order to ensure total control of the optimal examination conditions.

In order to carry out examinations of this kind or detection of the position of the eye, it is known to use an illumination system, for example a laser beam, and/or an image capture system, such as a camera, which must be pointed on the person's eye. However, in portable display equipment, the presence of one or more screens in front of the person's eyes prevents such an illumination system or image capture system from being placed in an appropriate position, in front of the person's eyes.

According to a particularly advantageous feature of the invention, it has been envisaged to place such illumination or image capture systems outside of the person's field of vision, and to point them on an eye by way of a reflection on a semi-reflective surface placed in front of the person's eye or eyes. The semi-reflective surface may be formed, for example, by the surface of the screen itself, or any other semi-reflective surface placed in front of the screen. It may, if necessary, have a particular orientation that is different from the orientation of the screen. The semi-reflective surface does not impair the view of the screen, but makes it possible, for example when the screen emits no or little light, to reflect a light beam, such as a laser beam, in order to point it onto the eye, or to reflect an image of the eye in order to capture it on a camera.

Figure 3:
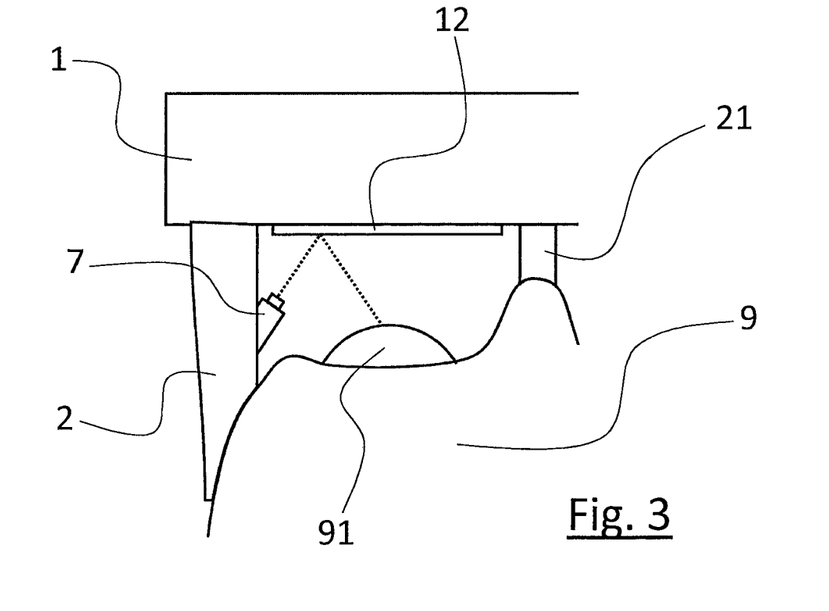
FIG. 3 is a schematic partial cross-section, according to a horizontal plane, of the head of a person wearing the display equipment of FIG. 2.

FIGS. 2 and 3 show an embodiment of this technical solution. In FIG. 2, it is possible to see that the closure lips 2 of the mask 1 bear a miniature camera 7 which is pointed towards the screen 12. The camera 7 is also visible in FIG. 3, which is a schematic cross-section, according to a horizontal plane, showing part of the head 9 of a person wearing the mask 1. As shown by the dashed lines representing the pointing of the camera 7, this makes it possible to capture images of the eye 91 which are reflected in the screen 12 that forms a semi-reflective surface. The camera 7 can thus, for example, capture images that represent the position of the eye, the size of the pupil, or the position of the eyelids.

This camera may be used, for example, at a moment when the screen 12 is switched off, or at a moment when the screen emits only weak and uniform light, sufficient for illuminating the eye but not disturbing the reflection of the image of the eye, or indeed at a moment when only a zone of the screen that is not used for the reflection is emitting light, in order to illuminate the eye, the zone of the screen used for the reflection being switched off. In other cases, the illumination allowing for use of the camera can be achieved by means of electroluminescent diodes placed beside the screens.

In other embodiments, it is possible to point a laser beam onto the eye, by means of a reflection on the screen or on a semi-reflective surface placed in front of the screen, and to capture, in the same manner, the reflection, by the eye, of the laser beam.

It should be noted that such a use of the screen placed in front of the eye as a semi-reflective surface, or the use of a semi-reflective surface placed in front of the screen, in order to point an illumination system or an image capture system on the eye, can advantageously be implemented in all types of portable display equipment comprising at least one display screen which is intended to be placed in front of at least one eye of a person, irrespective of the other features of the display equipment described in the present application.

Portable display equipment comprising at least one display screen that is intended to be placed in front of at least one eye of a person, and comprising at least one semi-reflective surface that is intended to be placed in front of at least one eye of the person, and at least one illumination and/or image capture device, pointed onto the eye, by means of a reflection on the semi-reflective surface, is thus particularly advantageous.

In this case, the semi-reflective surface can advantageously be either the surface of the screen itself, or a semi-reflective surface placed in front of the screen.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A device for exploration of a human visual system, comprising:
   portable display equipment comprising:
      at least one display screen configured to be placed in front of at least one eye of a person,
      closure lips that surround at least said display screen or one of said display screens and comprise a free edge that is configured to be applied against the person's skin, around his eye or his eyes in front of said screen, said free edge comprising at least one electrode for measuring an electrical potential, which electrode is intended to be applied against skin of the person, and, at least one free electrode for measuring an electrical potential, which electrode is connected, with a connecting wire, to a connector, forming a mechanical and electrical connection, the connector borne by said display equipment, between one of said display screens and said free edge of the closure lips surrounding said display screen, so that the at least one free electrode is configured to be positioned in contact with the person independently from the closure lips.

2. The exploration device according to claim 1, wherein said display equipment comprises two display screens which are each configured to be placed in front of one of the eyes of said person, and wherein said closure lips surround each of said screens.

3. The exploration device according to claim 1, wherein said closure lips comprise means for retaining optical lenses in front of at least one of said screens.

4. The exploration device according to claim 1, further comprising a retaining strap for said display equipment, which strap is configured to be passed behind a head of said person, said retaining strap bearing at least one electrode for measuring the electrical potential.

5. The exploration device according to claim 1, wherein said connector is located inside a space defined by the closure lips and is borne by the end of a second wire, the second wire passing through the closure lips via a hole, a length of the second wire being located inside the space defined by the closure lips being variable by sliding of the second wire through the said hole.

6. The exploration device according to claim 1, further comprising an acquisition system that is capable of synchronizing data measured by the electrode with visual stimulations produced by said screen.

7. The exploration device according to claim 6, wherein said acquisition system comprises means for amplifying signals measured by the electrode, means for filtering said signals, and means for converting analog signals into digital signals.

8. The exploration device according to claim 1, further comprising an audio output that is configured to communicate instructions to said person.

9. The exploration device according to claim 1, further comprising at least one input peripheral.

10. The exploration device according to claim 1, further comprising at least one computer that is remote from said display equipment, and means for communicating between said display equipment and said remote computer.

11. The exploration device according to claim 1, wherein said portable display equipment comprises at least one semi-reflective surface that is configured to be placed in front of at least one eye) of the person, and at least one of an illumination or image capture device, pointed in a direction of said eye, by means of a reflection on said semi-reflective surface.

12. The exploration device according to claim 11, wherein said semi-reflective surface is formed by the surface of said display screen.

13. The exploration device according to claim 11, wherein said semi-reflective surface is placed in front of the surface of said display screen.

14. The exploration device according to claim 11, wherein said illumination or image capture device is a camera.

15. The exploration device according to claim 11, wherein said illumination or image capture device comprises a laser emitter and means for capturing the reflection, on the eye, of a laser beam emitted by said laser emitter.

* * * * *